US008119419B2

(12) United States Patent
Stroup

(10) Patent No.: US 8,119,419 B2
(45) Date of Patent: Feb. 21, 2012

(54) CHECK VALVE-LESS FLUID-TRANSFER COLLECTION ASSEMBLY AND METHOD OF USING THE SAME

(75) Inventor: David Karl Stroup, La Jolla, CA (US)

(73) Assignee: Infusion Innovations, Inc., La Jolla, CA (US)

(*) Notice: Subject to any disclaimer, the term of this patent is extended or adjusted under 35 U.S.C. 154(b) by 88 days.

(21) Appl. No.: 12/549,214

(22) Filed: Aug. 27, 2009

(65) Prior Publication Data

US 2010/0050791 A1    Mar. 4, 2010

Related U.S. Application Data

(60) Provisional application No. 61/092,941, filed on Aug. 29, 2008.

(51) Int. Cl.
*G01N 1/14* (2006.01)
*G01N 33/00* (2006.01)
(52) U.S. Cl. ......... 436/180; 436/174; 422/68.1; 422/50; 73/61.41; 73/53.01; 73/864.34
(58) Field of Classification Search .................. 436/180, 436/174; 73/61.41, 53.01, 864.34, 864, 863; 422/68.1, 50
See application file for complete search history.

(56) References Cited

U.S. PATENT DOCUMENTS

| | | |
|---|---|---|
| 3,640,388 A | 2/1972 | Ferrari |
| 4,014,328 A | 3/1977 | Cluff et al. |
| 4,685,472 A | 8/1987 | Muto |
| 5,029,583 A | 7/1991 | Meserol et al. |
| 5,096,669 A | 3/1992 | Lauks et al. |
| 5,505,212 A | 4/1996 | Keljmann et al. |
| 5,595,187 A | 1/1997 | Davis |
| 5,636,640 A | 6/1997 | Staehlin |
| 5,800,779 A | 9/1998 | Johnson |

(Continued)

FOREIGN PATENT DOCUMENTS

JP    11-183468 A    7/1999

(Continued)

OTHER PUBLICATIONS

International Search Report and Written Opinion issued in PCT/US2009/055231 on Apr. 8, 2010, 10 pages.

*Primary Examiner* — Christine T Mui
(74) *Attorney, Agent, or Firm* — Stephen C. Beuerle; Procopio Cory Hargreaves & Savitch LLP

(57) ABSTRACT

A method of using a fluid transfer collection assembly includes providing an assembly including a base, a test media carried by the base, an inlet for receiving a sample fluid, an outlet, a fluid transfer path located between the inlet and the outlet, a movable first finger mechanism, a movable second finger mechanism operatively coupled to the movable first finger mechanism; first moving at least one of the first mechanism and the second mechanism relative to the path so that at least one of the first mechanism and the second mechanism engage the path to draw the sample fluid into the path; and then moving at least one of the first mechanism and the second mechanism relative to the path so that at least one of the first mechanism and the second mechanism engage the path to transfer the sample fluid through the path to the test media.

17 Claims, 2 Drawing Sheets

U.S. PATENT DOCUMENTS

| | | |
|---|---|---|
| 6,258,045 B1 | 7/2001 | Ray et al. |
| 6,426,213 B1 | 7/2002 | Eisenson |
| 6,660,527 B2 | 12/2003 | Stroup |
| 2001/0007926 A1 | 7/2001 | Trudil |
| 2001/0008614 A1 | 7/2001 | Aronowitz |
| 2004/0146848 A1* | 7/2004 | Kislev et al. .............. 435/4 |

FOREIGN PATENT DOCUMENTS

| | | |
|---|---|---|
| JP | 11-183469 A | 7/1999 |
| KR | 10-2008-0040690 A | 5/2008 |
| WO | 98-44331 A1 | 10/1998 |

* cited by examiner

CHECK VALVE-LESS FLUID-TRANSFER COLLECTION ASSEMBLY AND METHOD OF USING THE SAME

CROSS-REFERENCE TO RELATED APPLICATION

This application claims the benefit of provisional patent application 61/092,941, filed Aug. 29, 2008 under 35 U.S.C. 119(e). This provisional patent application is incorporated by reference herein as though set forth in full.

FIELD OF THE INVENTION

The present invention is in the field of fluid-transfer collection assemblies.

BACKGROUND OF THE INVENTION

Collection kits used for testing one or more analytes of a sample include multiple separate components such as a pipettes, collection tubes, vials or ampoules containing needed diluents or reagents, and test media devices. Because these collection kits have so many separate pieces, in most cases, use of such collection kits has been limited to a laboratory. Simple tests may be performed outside of the laboratory using only test media devices, but these test media devices are limited as to the types of tests that can be performed. More elaborate tests require diluents, pipettes, collection tubes, etc., and are difficult and awkward to perform outside of the laboratory.

Fluid transfer collection assemblies including check valves have been designed in the past. An inlet check valve allows one-way flow of a sample into a sample collection and mixing zone. After the sample has been drawn into the sample collection and mixing zone, and mixed with a reagent, the mixed sample and reagent mixture is transferred through an outlet check valve, to a testing zone. Check valves are an effective way to provide one-way transfer of fluid in such an assembly, however, they add expense to the cost of the assembly.

Accordingly, a need exists for a check valve-less fluid transfer collection assembly that does not include numerous separate pieces, is easy to use, can be used for multiple different types of tests and can be used in and outside a laboratory.

SUMMARY OF INVENTION

Accordingly, an aspect of the invention involves a fluid transfer collection assembly that does not include check valves for one-way transfer of fluid through the assembly. The assembly includes a slidable first finger mechanism and a slidable second finger mechanism operatively coupled together. The assembly includes a base, a test media carried by the base, a silicone pump tube carried by the base that fluid is transferred through, and a collection tube carried by a distal end of the assembly for drawing a sample into the silicone pump tube. The first finger mechanism and the second finger mechanism are movable relative to and engage the silicone pump tube to draw a sample into the silicone pump tube via the collection tube, and transfer the sample through the silicone pump tube to the test media.

Another aspect of the invention involves a method of using a fluid transfer collection assembly. The method includes providing a fluid transfer collection assembly including a base, a test media carried by the base, an inlet for receiving a sample fluid, an outlet, a fluid transfer path located between the inlet and the outlet, a movable first finger mechanism, a movable second finger mechanism operatively coupled to the movable first finger mechanism; first moving at least one of the first finger mechanism and the second finger mechanism relative to the fluid transfer path so that at least one of the first finger mechanism and the second finger mechanism engage the fluid transfer path to draw the sample fluid into the fluid transfer path; then moving at least one of the first finger mechanism and the second finger mechanism relative to the fluid transfer path so that at least one of the first finger mechanism and the second finger mechanism engage the fluid transfer path to transfer the sample fluid through the fluid transfer path to the test media.

A further aspect of the invention involves a fluid transfer collection assembly. The fluid transfer collection assembly includes a base; a test media carried by the base; an inlet for receiving a sample fluid; an outlet; a fluid transfer path located between the inlet and the outlet; a movable first finger mechanism; a movable second finger mechanism operatively coupled to the movable first finger mechanism; and wherein the first finger mechanism and the second finger mechanism movable relative to the fluid transfer path and each other so that at least one of the first finger mechanism and the second finger mechanism engage the fluid transfer path to draw the sample fluid into the fluid transfer path and transfer the sample fluid through the fluid transfer path to the test media.

Other and further objects, features, aspects, and advantages of the present inventions will become better understood with the following detailed description of the accompanying drawings.

DESCRIPTION OF THE PREFERRED EMBODIMENT

Figure 1:
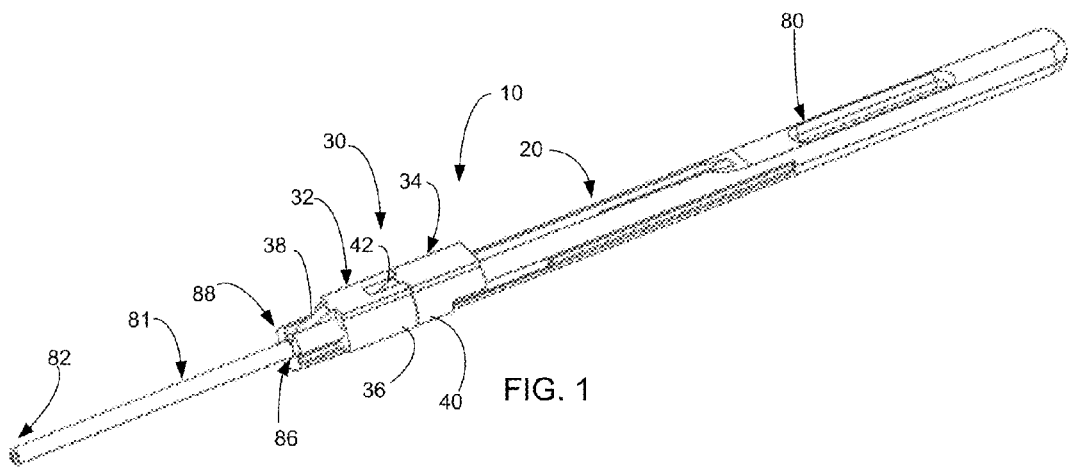
FIG. 1 is perspective view of a check valve-less fluid transfer collection assembly constructed in accordance with an embodiment of the invention.

With reference to FIGS. 1-6, an embodiment of a check valve-less fluid transfer collection assembly 10, and method of using the same will now be described. Further below, the collection assembly 10 will be described as an optical assay test device in an optical assay test method; however, the collection assembly 10 may be used in other devices, processes, and applications where delivery of one or more sample fluids to a collection area is desired. Although the check valve-less fluid transfer collection assembly 10 will be described in terms of transferring a sample fluid to a test media, in alternative embodiments, the check valve-less fluid transfer collection assembly 10 may be used for mixing two or more fluids (e.g., mixing a reagent with the biological fluid), and transferring the two or more fluids to the test media.

The collection assembly 10 includes an elongated plastic base 20 that carries a fluid transfer mechanism 30 comprised of a movable/slidable first finger mechanism 32 and a movable/slidable second finger mechanism 34 slidably carried by the base 20. The movable first finger mechanism 32 includes a slidable section 36 and a flexible resilient engagement finger 38. Similarly, the second finger mechanism 34 includes a slidable section 40 and a flexible resilient engagement finger 42. The second finger mechanism 34 is coupled to the first finger mechanism 32 via a limiting mechanism. The limiting mechanism limits movement of the second finger mechanism 34 relative to the first finger mechanism 32 and vice versa in a manner described below.

Figure 2:
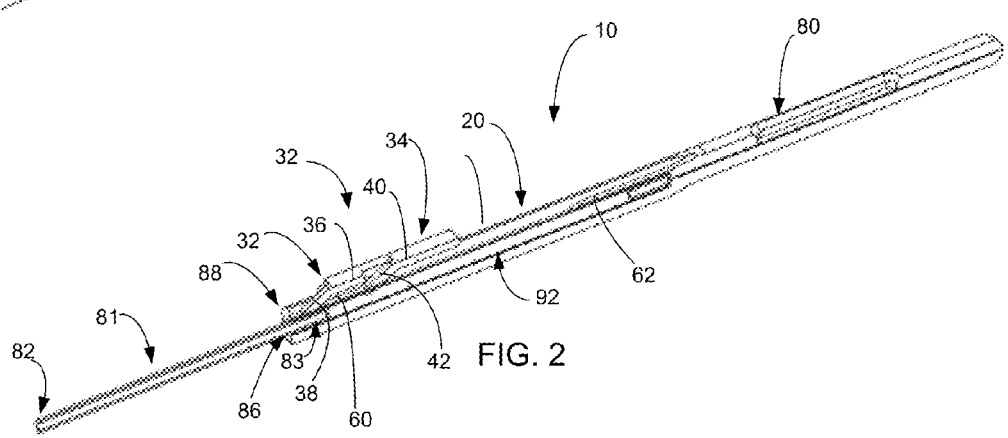
FIG. 2 is a perspective cross-sectional view of the check valve-less fluid transfer collection assembly of FIG. 1, and shows a slidable first finger mechanism in a home position and a slidable second finger mechanism in a home position.
Figure 4:
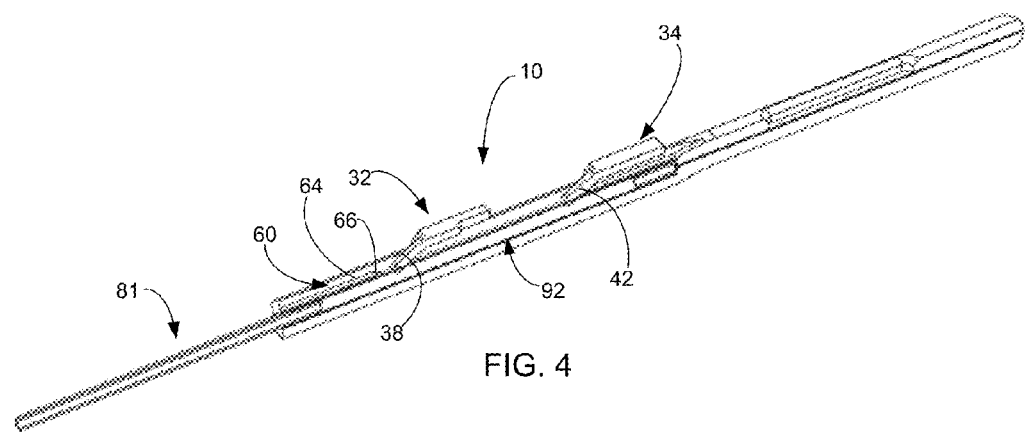
FIG. 4 is a perspective cross-sectional view of the check valve-less fluid transfer collection assembly of FIG. 1, and shows the slidable first finger mechanism slid rearwardly relative to the home position and the slidable second finger mechanism slid rearwardly relative to the position shown in FIG. 3.
Figure 5:
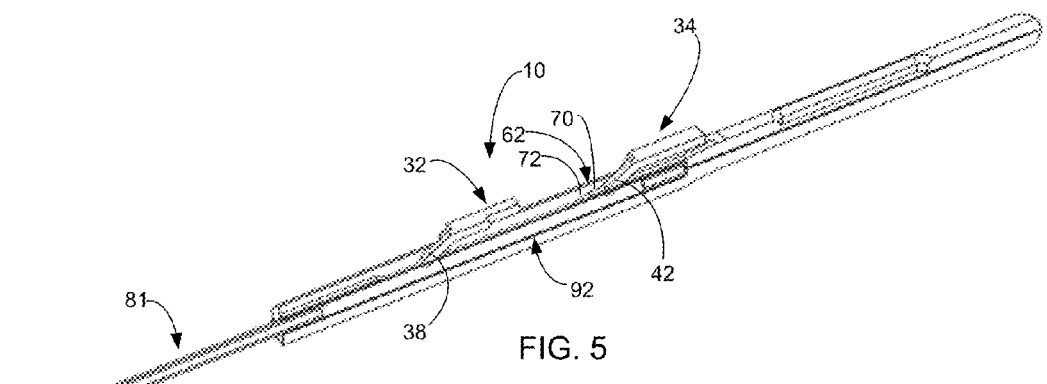
FIG. 5 is a perspective cross-sectional view of the check valve-less fluid transfer collection assembly of FIG. 1, and shows the slidable first finger mechanism slid rearwardly relative to the position shown in FIG. 4 and the slidable second finger mechanism slid rearwardly relative to the position shown in FIG. 4.

As shown in FIG. 2, the collection assembly 10 includes a distal ramp assembly 60 and a proximal ramp assembly 62. As best shown in FIG. 4, the distal ramp assembly 60 includes an upper section 64 and a ramp 66. Similarly, as best shown in FIG. 5, the proximal ramp assembly 62 includes an upper section 70 and a ramp 72.

The collection assembly 10 includes one or more test media carried by the base 20 in a test media section 80. In the embodiment shown, the one or more test media may include visual indicia to visually indicate the presence, absence, or concentration of a target analyte or other target object(s). The test media may include one or more of the following: base strip(s), sample pad(s), conjugate pad(s), membrane(s), and absorbent pad(s).

The collection assembly 10 includes a collection tube 81 having a distal end 82 and a proximal end 83 carried by an inlet 86 at a distal end 88 of the collection assembly 10 for drawing a sample into the collection assembly 10. A flexible silicone pump tube 92 inside of the base 20 receives the sample fluid from the collection tube 81. The collection tube 81 and the silicone pump tube 92 form a fluid path for the sample fluid to the test media section 80. The first finger mechanism 32 and the second finger mechanism 34 are movable/slidable relative to and engage the silicone pump tube 92 to draw a sample into the silicone pump tube 92 via the collection tube 81, and transfer the sample through the silicone pump tube 92 to the test media section 80.

The collection assembly 10 will now be described in use as an optical assay test device in an exemplary optical assay method of use. The collection assembly 10 and method of use may be used in applications such as, but not by way of limitation, drug screening, chemical analysis, crime/accident scene investigations, ground water testing (EPA), and livestock testing.

With reference to FIG. 1, the collection tube 81 normally includes (or starts with) the slidable first finger mechanism 32 in a home position and a slidable second finger mechanism 34 in a home position as shown. When the slidable first finger mechanism 32 is in the home position, the flexible resilient engagement finger 38 is urged upwards by and rests on upper section 64 of the distal ramp assembly 60. When the slidable second finger mechanism 34 is in the home position, the flexible resilient engagement finger 42 engages the silicone pump tube 92. The distal end 82 of the collection tube 81 may be put in communication with a fluid sample. The sample may be any fluid medium such as, but not by way of limitation, a gas, a liquid, a suspension, an extracted or dissolved sample, or a supercritical fluid, as long as some flow properties exist in the sample. The sample may include one or more target analytes of interest for detection. Example analytes include, but not by way of limitation, antigens, antibodies, receptors, ligands, chelates, proteins, enzymes, nucleic acids, DNA, RNA, pesticides, herbicides, inorganic or organic compounds or any material for which a specific binding reagent may be found.

Figure 3:
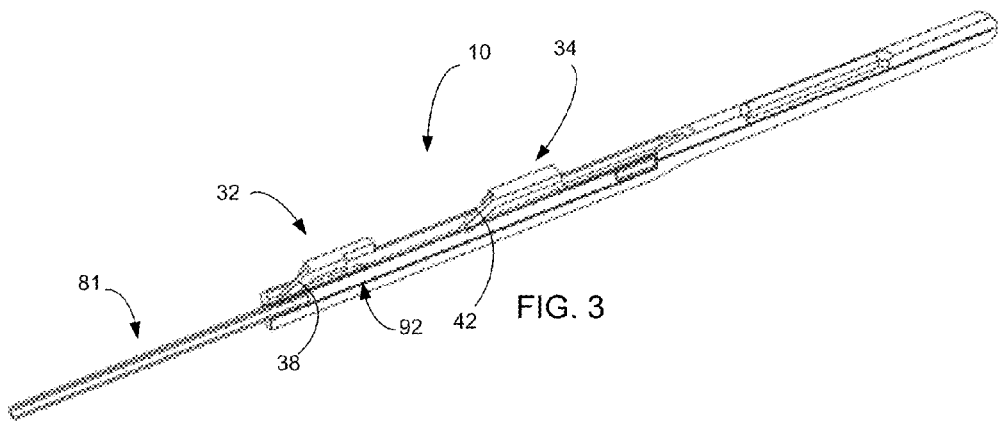
FIG. 3 is perspective cross-sectional view of the check valve-less fluid transfer collection assembly of FIG. 1, and shows the slidable first finger mechanism in a home position and the slidable second finger mechanism slid rearwardly relative to the home position.

The second finger mechanism 34 is depressed/engaged with one's thumb and slid rearwardly along opposite tracks on opposite sides of the elongated plastic base 20 to a position such as that shown in FIG. 3. Because the flexible resilient engagement finger 42 engages the silicone pump tube 92 during this rearward movement of the second finger mechanism 34, a vacuum pumping action is created in the silicone pump tube 92.

The vacuum force in the silicone pump tube 92 causes the sample fluid to flow through the collection tube 81 and into the silicone pump tube 92, past the first finger mechanism 32, which includes its flexible resilient engagement finger 38 urged upwards by and resting on upper section 64 of the distal ramp assembly 60, into this region of the silicone pump tube 92 between the first finger mechanism 32 and the second finger mechanism 34. In an embodiment of the collection assembly 10, where a second fluid is disposed in this region of the silicone pump tube 92 between the first finger mechanism 32 and the second finger mechanism 34, the sample and the second fluid may mix. However, where only the sample fluid is drawn and collected in the collection assembly 10, the sample fluid alone is disposed in this region of the silicone pump tube 92 between the first finger mechanism 32 and the second finger mechanism 34.

With reference to FIGS. 4 and 5, as the second finger mechanism 34 is slid further rearwardly, the limiting mechanism, which couples and limits the range of movement of the second finger mechanism 34 relative to the first finger mechanism 32, pulls the first finger mechanism 32 rearwardly once the second finger mechanism 34 reaches a certain distance relative to the first finger mechanism 32. As the first finger mechanism 32 is pulled/moved rearwardly, the flexible resilient engagement finger 38 slides off of the upper section 64 and down the ramp 66 of the distal ramp assembly 60. Once first finger mechanism 32 is pulled/moved rearwardly to a position where the flexible resilient engagement finger 38 has completely slid off of the ramp 66, the flexible resilient engagement finger 38 engages the silicone pump tube 92. Fluid (e.g., sample fluid or mixed sample fluid and second fluid) becomes trapped in the silicone pump tube 92 between the flexible resilient engagement finger 38 of the first finger mechanism 32 and the flexible resilient engagement finger 42 of the second finger mechanism 34. This trapped fluid is moved rearwardly in the silicone pump tube 92 as the first finger mechanism 32 and the second finger mechanism 34 move rearwardly.

Further rearward movement of the second finger mechanism 34 causes the flexible resilient engagement finger 42 of the second finger mechanism 34 to engage the ramp 72 of the proximal ramp assembly 62. Further rearward movement of the second finger mechanism 34 causes the flexible resilient engagement finger 42 to ride up the ramp 72 and onto the upper section 70 of the proximal ramp assembly 62. In this position, the flexible resilient engagement finger 38 no longer engages/blocks the silicone pump tube 92.

Figure 6:
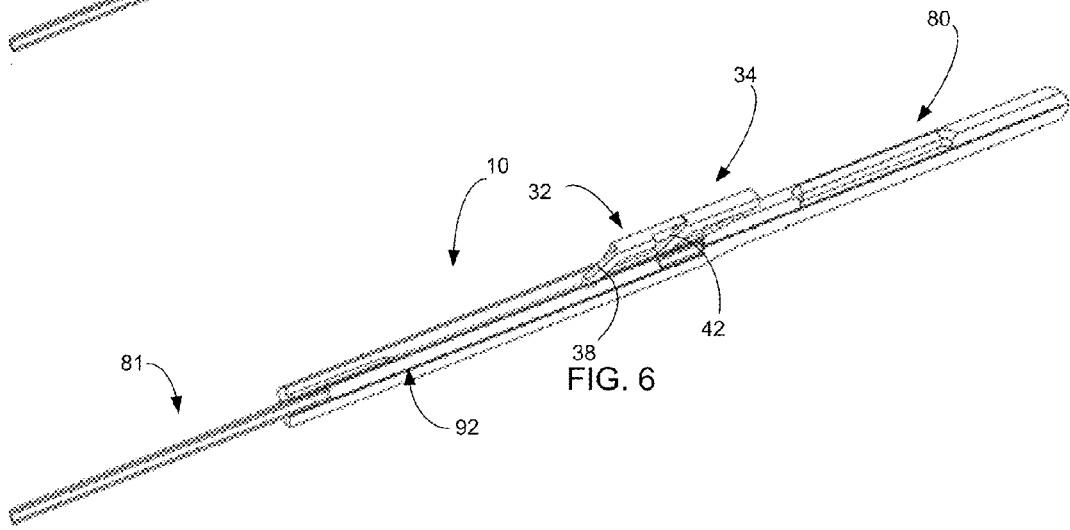
FIG. 6 is a perspective cross-sectional view of the check valve-less fluid transfer collection assembly of FIG. 1, and shows the slidable first finger mechanism slid rearwardly relative to the position shown in FIG. 5 and the slidable second finger mechanism slid rearwardly relative to the position shown in FIG. 5.

With reference to FIG. 5, the first finger mechanism 32 is engaged with the user's thumb and moved rearwardly to a position such as that shown in FIG. 6. This causes the flexible resilient engagement finger 38 of the first finger mechanism 32 to impart rearward-directed pressure on the fluid so that the fluid flows past the second finger mechanism 34 (now up and out-of-the way on ramp 62) to the test media section 80, and the one or more test media. Visual indicia of the one or more test media may indicate the presence, absence, or concentration of a target analyte for the optical assay method. In an embodiment of the invention, multiple test media are used to test for the presence, absence, or concentration of a target analyte of interest.

Numerous features, implementations, and embodiments of the collection assembly 10 will now be described. The collection assembly 10 may be used more than once to perform the same test, different tests, or may be disposed of after single use. Different collection assemblies 10 may be used to perform different tests. The collection assembly 10 may be used to test for the presence, absence, or concentration of one or more analytes. The collection assembly 10 may be held and operated with a single hand of a user and with the thumb of the same hand. The collection assembly 10 is especially advantageous in that fluid transfer or fluid transfer/mixing steps can all be done with a single hand of the user.

In one or more embodiments of the collection assembly 10, the collection tube 81 may have one or more of the following: the collection tube 81 may be fixed to the inlet 86, the collection tube 81 may be retractable, the collection tube 81 may not be retractable, the collection tube 81 may lock to the inlet 86, the collection tube 81 may not lock to the inlet 86, the collection tube 81 may detachably connect to the inlet 86, the collection tube 81 may include or be replaced with one or more wicks, sponges, open-cell foams, porous materials, or other absorbent materials.

The assembly 10 is advantageous in that it can be gripped in one hand and by the simple engaging and pulling action of one's thumb on the first finger mechanism 32 and the second finger mechanism 34, fluid can be transferred from the collection tube 81, through the silicone pump tube 92, and to the one or more test media in the test media section 80. The assembly 10 is advantageous because it has fewer parts that other pump designs; no check valves are required. Because the unit is so simple to use, the assembly 10 may be used by the user for testing in the field, in the lab, and in the home for a wide variety of applications.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

I claim:

1. A method of using a fluid transfer collection assembly, comprising:

providing a fluid transfer collection assembly including a base, a test media carried by the base, an inlet for receiving a sample fluid, an outlet, a fluid transfer path located between the inlet and the outlet, a movable and slidable first finger mechanism, a movable and slidable second finger mechanism operatively coupled to the movable first finger mechanism;

first moving at least one of the first finger mechanism and the second finger mechanism relative to the fluid transfer path so that at least one of the first finger mechanism and the second finger mechanism engage the fluid transfer path to draw the sample fluid into the fluid transfer path;

then moving at least one of the first finger mechanism and the second finger mechanism relative to the fluid transfer path so that at least one of the first finger mechanism and the second finger mechanism engage the fluid transfer path to transfer the sample fluid through the fluid transfer path to the test media, wherein the base includes a ramp assembly adjacent the inlet, the first finger mechanism includes a first flexible resilient engagement finger, and the second finger mechanism includes a second flexible resilient engagement finger, and the method further including starting with the first finger mechanism and the second finger mechanism in a home position, the home position including the first flexible resilient engagement finger urged upwards by the ramp assembly and the second flexible resilient engagement finger engaging the fluid transfer path.

2. The method of claim 1, wherein first moving includes moving the second finger mechanism rearwardly relative to the first finger mechanism so that the second flexible resilient engagement finger engages the fluid transfer path to draw the sample fluid past through the inlet and past the first finger mechanism, and into the fluid transfer path.

3. The method of claim 1, further including a second fluid in the fluid transfer path and first moving further includes drawing the sample fluid into the fluid transfer path and mixing with the second fluid in the fluid transfer path, and then moving further includes transferring the mixed sample fluid and second fluid through the fluid transfer path and the outlet to the test media.

4. The method of claim 1, wherein moving includes moving in an inlet-to-outlet longitudinal direction along the fluid transfer path.

5. The method of claim 1, wherein the fluid transfer path includes a silicone pump tube.

6. The method of claim 1, wherein the inlet and the outlet are check valve-less.

7. The method of claim 1, further including a sample tube having a proximal end coupled to the inlet and a distal end, and the method further includes communicating the distal end of the sample tube with the sample fluid to draw the sample fluid into the interior of the fluid transfer path.

8. The method of claim 7, wherein the sample tube is at least one of fixed to the inlet, retractable, not retractable, locked to the inlet, not locked to the inlet, and detachably connectable to the inlet.

9. The method of claim 1, further including at least one of a wick, sponge, open-cell foam, porous material, and an absorbent material connected to the inlet, and the method further includes communicating at least one of the wick, sponge, open-cell foam, porous material, and an absorbent material with the sample fluid to draw the sample fluid into the interior of the fluid transfer path.

10. The method of claim 1, wherein the method is an assay test method, the sample fluid includes an analyte of interest for assay testing, the second fluid is a reagent, and the test media visually indicates the presence or absence of an analyte of interest.

11. The method of claim 1, wherein the method is a test method for testing at least one of drug screening, chemical analysis, crime/accident scene investigations, ground water testing (EPA), and livestock testing.

12. The method of claim 1, wherein the sample fluid is a fluid medium of at least one of a gas, a liquid, a suspension, an extracted or dissolved sample, and a supercritical fluid.

13. The method of claim 1, wherein the sample fluid includes a sample including one or more target analytes of interest for detection.

14. The method of claim 13, wherein the one or more target analytes of interest include at least one of antigen, antibody, receptor, ligands chelate, protein, enzyme, nucleic acid, DNA, RNA, pesticide, herbicide, inorganic compound, organic compounds, a material for which a specific binding reagent exists.

15. The method of claim 1, wherein test media indicates at least one of presence, absence, and concentration of one or more analytes.

16. A method of using a fluid transfer collection assembly, comprising:
  providing a fluid transfer collection assembly including a base, a test media carried by the base, an inlet for receiving a sample fluid, an outlet, a fluid transfer path located between the inlet and the outlet, a movable and slidable first finger mechanism, a movable and slidable second finger mechanism operatively coupled to the movable first finger mechanism;
  first moving at least one of the first finger mechanism and the second finger mechanism relative to the fluid transfer path so that at least one of the first finger mechanism and the second finger mechanism engage the fluid transfer path to draw the sample fluid into the fluid transfer path;
  then moving at least one of the first finger mechanism and the second finger mechanism relative to the fluid transfer path so that at least one of the first finger mechanism and the second finger mechanism engage the fluid transfer path to transfer the sample fluid through the fluid transfer path to the test media;
  further including a limiting mechanism coupling and limiting the range of movement of the second finger mechanism relative to the first finger mechanism so that when the second finger mechanism reaches a predetermined distance relative to the first finger mechanism, the limiting mechanism causes further movement of the second finger mechanism away from the first finger mechanism to pull the first finger mechanism, and then moving includes moving the second finger mechanism relative to the first finger mechanism so that the second finger mechanism reaches a predetermined distance relative to the first finger mechanism, causing the limiting mechanism to pull the first finger mechanism so that the first finger mechanism moves and engages the fluid transfer path to transfer the sample fluid through the fluid transfer path;
  wherein the base includes a ramp assembly adjacent the outlet, the first finger mechanism includes a first flexible resilient engagement finger, and the second finger mechanism includes a second flexible resilient engagement finger, and the then moving further includes moving the second finger mechanism so that the second flexible resilient engagement finger is urged upwards by the ramp assembly adjacent the outlet, and moving the first finger mechanism towards the second finger mechanism so that first flexible resilient engagement finger engages the fluid transfer path to transfer the sample fluid through the fluid transfer path and out the outlet and past the second finger mechanism to the test media.

17. A fluid transfer collection assembly, comprising:
  a base;
  a test media carried by the base;
  an inlet for receiving a sample fluid;
  an outlet;
  a fluid transfer path located between the inlet and the outlet;
  a movable and slidable first finger mechanism;
  a movable and slidable second finger mechanism operatively coupled to the movable first finger mechanism;
  wherein the first finger mechanism and the second finger mechanism movable relative to the fluid transfer path and each other so that at least one of the first finger mechanism and the second finger mechanism engage the fluid transfer path to draw the sample fluid into the fluid transfer path and transfer the sample fluid through the fluid transfer path to the test media,
  wherein the base includes a ramp assembly adjacent the inlet and a ramp assembly adjacent the outlet, and the first finger mechanism is operably associated with the ramp assembly adjacent the inlet to allow the sample fluid to be drawn into the fluid transfer path through the inlet and past the first finger mechanism and the second finger mechanism is operably associated with the ramp assembly adjacent the outlet to allow the sample fluid to be transferred through the fluid transfer path and through the outlet and past the second finger mechanism to the test media.

* * * * *